United States Patent [19]

Bode-Greuel

[11] Patent Number: 5,364,857
[45] Date of Patent: Nov. 15, 1994

[54] COMBINATION HAVING A NEUROPROTECTIVE EFFECT

[75] Inventor: Kerstin Bode-Greuel, Lohmar, Germany

[73] Assignee: Troponwerke GmbH & Co KG, Cologne, Germany

[21] Appl. No.: 976,791

[22] Filed: Nov. 16, 1992

[30] Foreign Application Priority Data

Nov. 26, 1991 [DE] Germany ............... 4138756

[51] Int. Cl.$^5$ ............... A61K 31/445; A61K 31/425; A61K 31/645; A61K 31/505
[52] U.S. Cl. ............... 514/259; 514/373
[58] Field of Search ............... 514/259, 373

[56] References Cited

U.S. PATENT DOCUMENTS

| | | |
|---|---|---|
| 3,041,344 | 6/1962 | Janssen . |
| 3,155,669 | 11/1964 | Janssen . |
| 3,155,670 | 11/1964 | Janssen . |
| 3,161,644 | 12/1964 | Janssen . |
| 3,919,425 | 11/1975 | Vidrio . |
| 4,335,127 | 6/1982 | Vandenberk et al. ............... 514/259 |
| 4,342,870 | 8/1982 | Kennis et al. ............... 544/282 |
| 4,522,945 | 6/1985 | Vandenberk et al. ............... 514/259 |
| 4,859,665 | 8/1989 | Garthoff et al. ............... 514/221 |
| 4,988,700 | 1/1991 | Traber et al. . |
| 5,070,102 | 12/1991 | Traber et al. . |
| 5,137,901 | 8/1992 | Junge et al. ............... 514/373 |
| 5,155,128 | 10/1992 | Traber et al. . |
| 5,200,410 | 4/1993 | Traber et al. . |

FOREIGN PATENT DOCUMENTS 0352613 1/1990 European Pat. Off. .
0360077 3/1990 European Pat. Off. .
4039631 6/1992 Germany .

OTHER PUBLICATIONS

Brogden et al., *Medline (NLM)*, 91176900, 1990.
Anonymous, *Medline (NLM)*, 89194457, 1989.
Doyle, *Medline (NLM)*, 91137288, 1990.
Journal of Cerebral Blood Flow and Metabolism 1, 155–185 (1981).
J. Pharmacol. Exp. Ther. 238, 248–253 (1986).
Molecular Pharmacology 16, 687–699 (1979).
J. Neurochem. 36, 220–226 (1981).
J. Pharmacol. Exp. Ther. 244, 1051–1065 (1988).
STN International, Karlsruhe; File "CA", Chemical Abstracts, vol. 115(17):180699; Blockade of 5-HT2 Receptors Protects Against Impairment . . ., 1991.
STN International, Karlsruhe; File "PHAR", Pharmaprojects; Copyright 1993; 2,4(1H,3H)-Quinazolinedione . . ., No. 006750.
*Brain Research*, 578 (1992), 1–7; "Ketanserin Reduces Neuronal Calcium Accumulation and Cell Death in the Hippocampus of the Mongolian Gerbil . . .".

*Primary Examiner*—Marianne M. Cintins
*Assistant Examiner*—William R. A. Jarvis
*Attorney, Agent, or Firm*—Sprung Horn Kramer & Woods

[57] ABSTRACT

The effect of neuroprotective 5-HT$_2$-receptorantagonistic 4-fluoro-phenyl compounds is intensified synergistically by 5-HT$_{1A}$-receptoragonistic aminomethyl-chromans. The combination of 5-HT$_{1A}$-receptoragonistic aminomethyl-chromans and 5-HT$_2$-receptorantagonistic 4-fluoro-phenyl compounds is suitable for the treatment of cerebral ischaemias.

3 Claims, 3 Drawing Sheets

COMBINATION HAVING A NEUROPROTECTIVE EFFECT

The invention relates to a synergistic combination of 5-$HT_{1A}$ receptor-agonistic aminomethyl-chromans with 5-$HT_2$ receptor-antagonistic 4-fluorophenyl compounds, their preparation and their use in neuroprotective medicaments, in particular for the treatment of cerebral ischaemic conditions.

Cerebral circulatory disorders result in a dying-off of brain cells. This neuronal degeneration, which often only occurs after a delay, leads to losses of function in the brain with neurological and/or psychic symptoms [Journal of Cerebral Blood Flow and Metabolism 1, 155–185 (1981)].

The causes of cerebral circulatory disorders can be vascular occlusions caused by arteriosclerosis, cerebral haemorrhages, inter alia after bursting of a vessel in the case of high blood pressure, but also ischaemias due to blood pressure decrease or embolism.

It is known that 5-$HT_{1A}$ receptor-agonistic active substances decrease the neuronal degeneration and the loss of function of the brain occurring as a consequence both in the case of prophylactic treatment and in the case of treatment carried out after cerebral ischaemia [German Offenlegungsschrift 3,542,794].

It has been found that 5-$HT_{1A}$ receptor-agonistic aminomethyl-chromans [component A] surprisingly increase the neuroprotective effect of 5-$HT_2$ receptor-antagonistic 4-fluoro-phenyl compounds in a synergistic manner.

5-$HT_{1A}$ receptor-agonistic aminomethyl-chromans (component A) in the context of the invention are understood as meaning serotonin-agonistic active substances of the general formula (I)

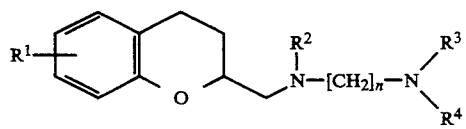

in which
R¹ represents hydrogen or alkoxy having up to 4 carbon atoms,
R² represents hydrogen or alkyl having up to 4 carbon atoms,
R³ represents hydrogen or alkyl having up to 4 carbon atoms,
R⁴ represents a group $SO_2R^5$ or

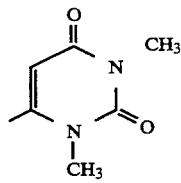

where
R⁵ denotes alkyl having up to 4 carbon atoms or phenyl or naphthyl which can be substituted by halogen or alkyl having up to 4 carbon atoms or R³ and R⁴, together with the nitrogen atom, form a ring of the formula

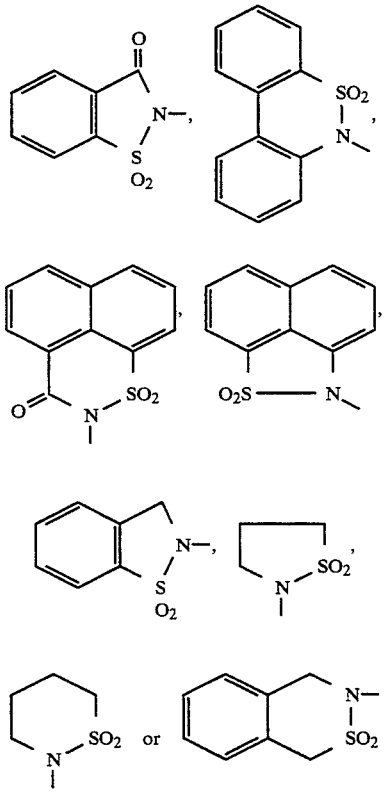

n represents a number 2, 3, 4 or 5,
if appropriate in an isomeric form, and their salts, which in the case of binding to 5-$HT_{1A}$ receptors have a binding strength of less than 1000 nmol/l.

Preferred aminomethyl-chromans of the formula (I) are those which in the case of binding to 5-$HT_{1A}$ receptors have a binding strength of less than 100 nmol/l.

Such active substances can be identified in the adenylate cyclase test ($EC_{50}$) [J. Pharmacol Exp. Ther. 238, 248–253 (1986)]. 5-$HT_{1A}$ ligands with agonistic or partially agonistic action inhibit forskolin-stimulated adenylate cyclase. Active substances which decrease the enzyme activity have a serotonin-agonistic or partially serotonin-agonistic action. The said adenylate cyclase test can be carried out, for example, as follows:

Rat hippocampus membranes are incubated under suitable conditions with α-$^{32}$P-ATP and forskolin in the absence and presence of compounds according to the invention. After stopping the reaction, the radiolabelled cyclic AMP is isolated and quantitatively determined. The enzyme activity is calculated from this, The binding strength (inhibition constant or $K_i$) is a measure of the interactions between an active substance and the 5-$HT_{1A}$ receptors [Molecular Pharmacology 16, 687–699 (1979); J. Neurochem. 36, 220–226, (1981)].

The binding strength can be determined, for example, as follows:

Calf hippocampus membranes are incubated with ³H-serotonin in the presence and absence of substances to be investigated. The reaction is stopped by filtration and the radioactivity remaining on the filters is measured. $IC_{50}$ values or inhibition constants $K_i$ are calculated from the displacement curves obtained.

Preferred aminomethyl-chromans of the general formula (I) are those in which $R^1$ represents hydrogen or methoxy,
$R^2$ represents hydrogen or propyl,
$R^3$ represents hydrogen or methyl,
$R^4$ represents a group $-SO_2R^5$, where
  $R^5$ denotes phenyl which is optionally substituted by fluorine or chlorine, or
$R^3$ and $R^4$, together with the nitrogen atom, form a group of the formula

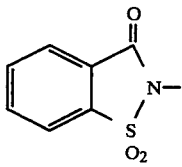

and
n denotes a number 4
if appropriate in an isomeric form, and their salts.

Particularly preferred aminomethyl-chroman compounds are the following:

(+)-, (−)- and (±)-2-[N-[4-(1,1-dioxido-3-oxo-2,3-dihydro-benzisothiazol-2-yl)butyl]aminomethyl]-8-methoxy-chroman and (+)-, (−)- and (±)-2-[N-[4-(1,1-dioxido-3-oxo-2,3-dihydro-benzisothiazol-2-yl)butyl]aminomethyl]-chroman and their salts.

5-HT$^2$ receptor-antagonistic 4-fluoro-phenyl compounds (component B) in the context of the invention are understood as meaning serotonin-antagonistic active substances of the general formula (II)

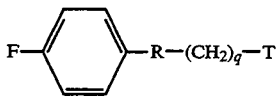   (II)

in which
R represents a group of the formula

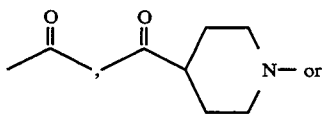

T represents a group of the formula

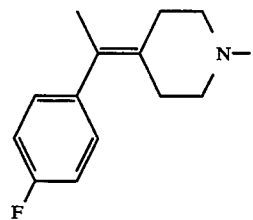

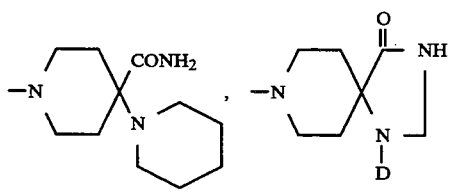

-continued

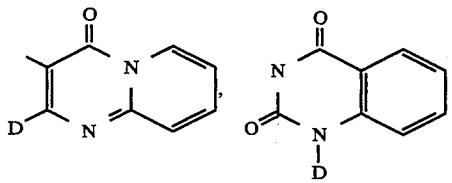

or

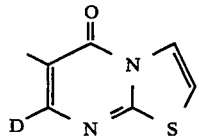

in which
D denotes hydrogen, $C_1$-$C_4$-alkyl or phenyl and
q represents a number 1, 2, 3 or 4
and their salts which in the case of binding to 5-HT$_2$ receptors have a binding strength of less than 1000 nmol/1, preferably 0.1 to 100 nmol/1, in particular less than 10 nmol/1.

Such active substances can be investigated in the phosphoinositol conversion test [J. Pharmacol. Exp. Ther. 244, 1051–1056 (1988)]. 5-HT$_2$ ligands with antagonistic action inhibit serotonin-stimulated phosphoinositol conversion. The whole test can be carried out, for example, as follows:

Cortex sections of 8-day-old rats are incubated under suitable conditions with $^3$H-myo-inositol and serotonin in the presence and absence of the compounds to be investigated. After stopping the reaction, the radiolabelled inositol phosphates are isolated and quantitatively determined.

Preferably, the following active substances may be mentioned as component B:

1-(4-fluorophenyl)-4-(4-piperidino-4-carbamoyl-piperidino)-1-butanone (INN: pipamperone); 4-phenyl-8-[3-(4-fluorobenzoyl)propyl]-1-oxo-2,4,8-triazaspiro[4,5]decane (INN:spiperone), 3-[2-[4-(4-fluorobenzoyl)-1-piperidinyl]-ethyl]-2,4-[1H, 3H]-quinazolinedione (INN: ketanserin), pirenperin (INN), ritanserin (INN) and pelanserin (INN).

Ketanserin is particularly preferred.

The 4-fluorophenyl compounds of the formula (II) are known per se [EP 13,612; BE 610, 830; U.S. Pat. Nos. 3,155,669; 3,155,670; 3,161,644; EP 37,265] and can be prepared by the processes described therein.

As already described, the 5-HT$_{1A}$ receptor-agonistic aminomethyl-chromans of the formula (I) increase in a synergistic manner the neuroprotective effect of 5-HT$_2$ receptor-antagonistic 4-fluoro-phenyl compounds of the formula (II) in such a way that, even in amounts at which the 5-HT$_{1A}$ agonist exhibits no neuroprotective effect, by combination with a suitable 5-HT$_2$ antagonist which likewise has no or only slight neuroprotective effect, the neuronal degeneration and the loss of function of the brain occurring as a consequence are clearly decreased both in the case of prophylactic treatment and in the case of treatment carried out after cerebral ischaemia.

Relative to one part by weight of the 5-HT$_{1A}$-receptor agonistic active substance (component A), 0.01 to 100 parts by weight, preferably 0.1 to 10 parts by weight, of the 5-HT$_2$ receptor-antagonistic active substance (component B) are employed. Combinations of (+)-, (−)- and (±)-2-[N-[4-(1,1-dioxido-3-oxo-2,3-dihydro-benzisothiazol-2-yl)butyl]aminomethyl]-8-methoxy-chroman and (+)-, (−)- and (±)-2-[N-[4-(1,1-dioxido-3-oxo-2,3-dihydro-benzisothiazol-2-yl)butyl]-aminomethyl]-chroman as component A with ketanserin as component B have a particularly good neuroprotective effect.

The combination of (+)-, (−)- and (±)-2-[N-[4-(1,1-dioxido-3-oxo-2,3-dihydro-benzisothiazol-2-yl)butyl]-aminomethyl]-chroman with ketanserin, very particularly preferably in an amount ratio of 1 to 10 parts by weight of ketanserin to 0.02 to 2 parts by weight of (+)-, (−)- and (±)-2-[N-[4-(1,1-dioxido-3-oxo-2,3-dihydro-benzisothiazol-2-yl)butyl]aminomethyl]-chroman, has a particularly good neuroprotective effect. It is therefore very particularly preferred.

The combination can be produced by dissolving the individual components in inert solvents which dissolve them and optionally mixing the combination with auxiliaries in a customary manner after evaporating off the solvent. Inert solvents which may be mentioned by way of example are alcohols such as ethanol or polyethylene glycol. The components can also be mixed as a solid.

The present invention also includes pharmaceutical preparations which, in addition to inert, non-toxic, pharmaceutically suitable auxiliaries and excipients contain the combination according to the invention or consist of the combination according to the invention, and processes for the production of these preparations.

The combination should be present in these preparations in a concentration of 0.1 to 99.5% by weight, preferably of 0.5 to 95% by weight, of the total mixture.

In addition to the combination, the pharmaceutical preparations can also contain other pharmaceutical active substances.

The abovementioned pharmaceutical preparations can be produced in a customary manner by known methods, four example using auxiliary(ies) or excipient(s).

In general, it has proved advantageous to administer the combination in total amounts of about 0.01 to about 100 mg/kg, preferably in total amounts of about 1 mg/kg to 50 mg/kg, of body weight every 24 hours, if appropriate in the form of several individual doses to achieve the desired result.

However, it may be advantageous to deviate from the amounts mentioned, in particular depending on the type and the body weight of the subject treated, on individual behaviour towards the medicament, the type and severity of the disease, the type of preparation and administration, and the time or interval at which administration takes place.

Figure 1:
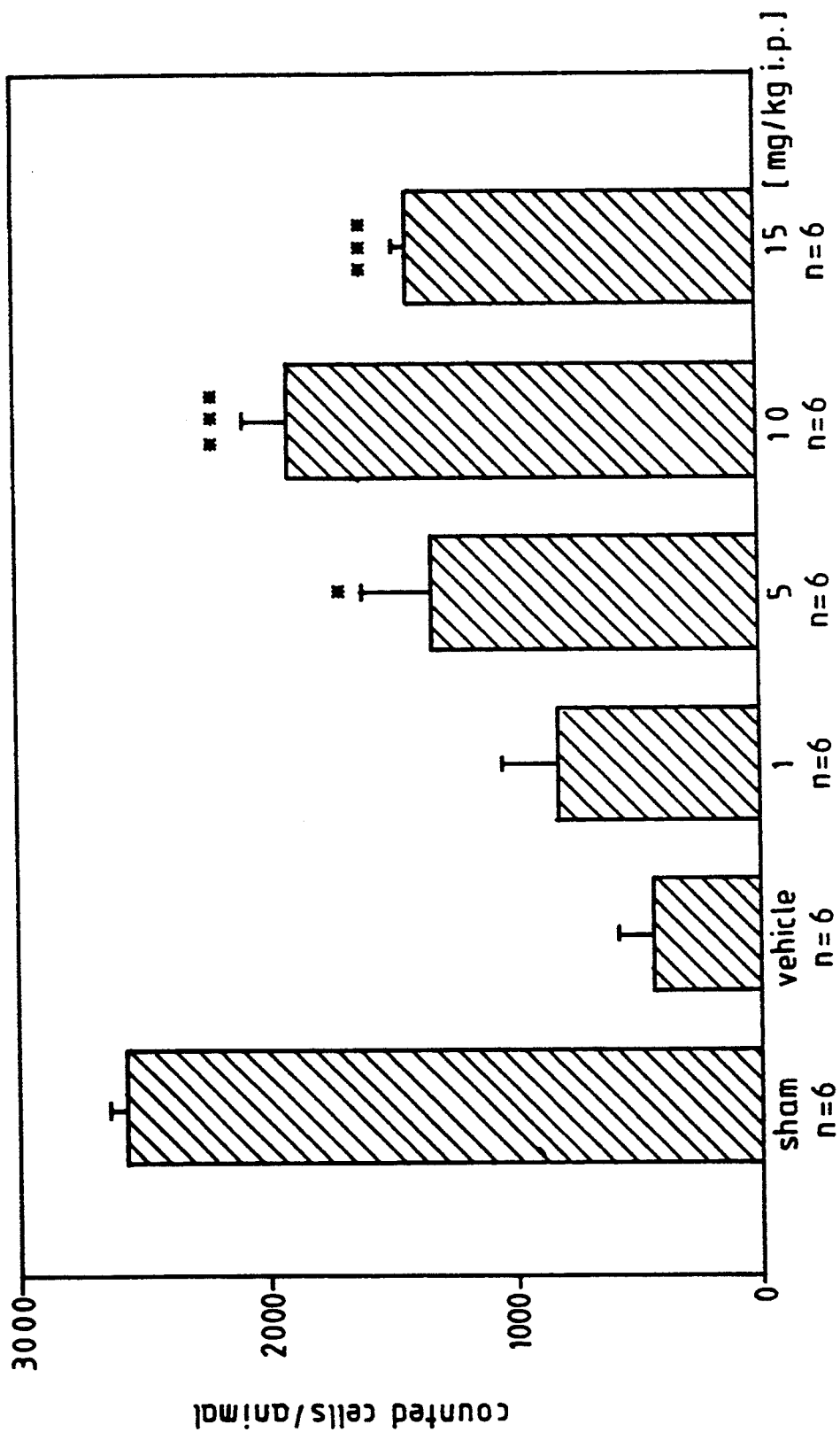
FIG. 1: shows Ketanserin (5-HT$_2$ antagonist)
Figure 2:
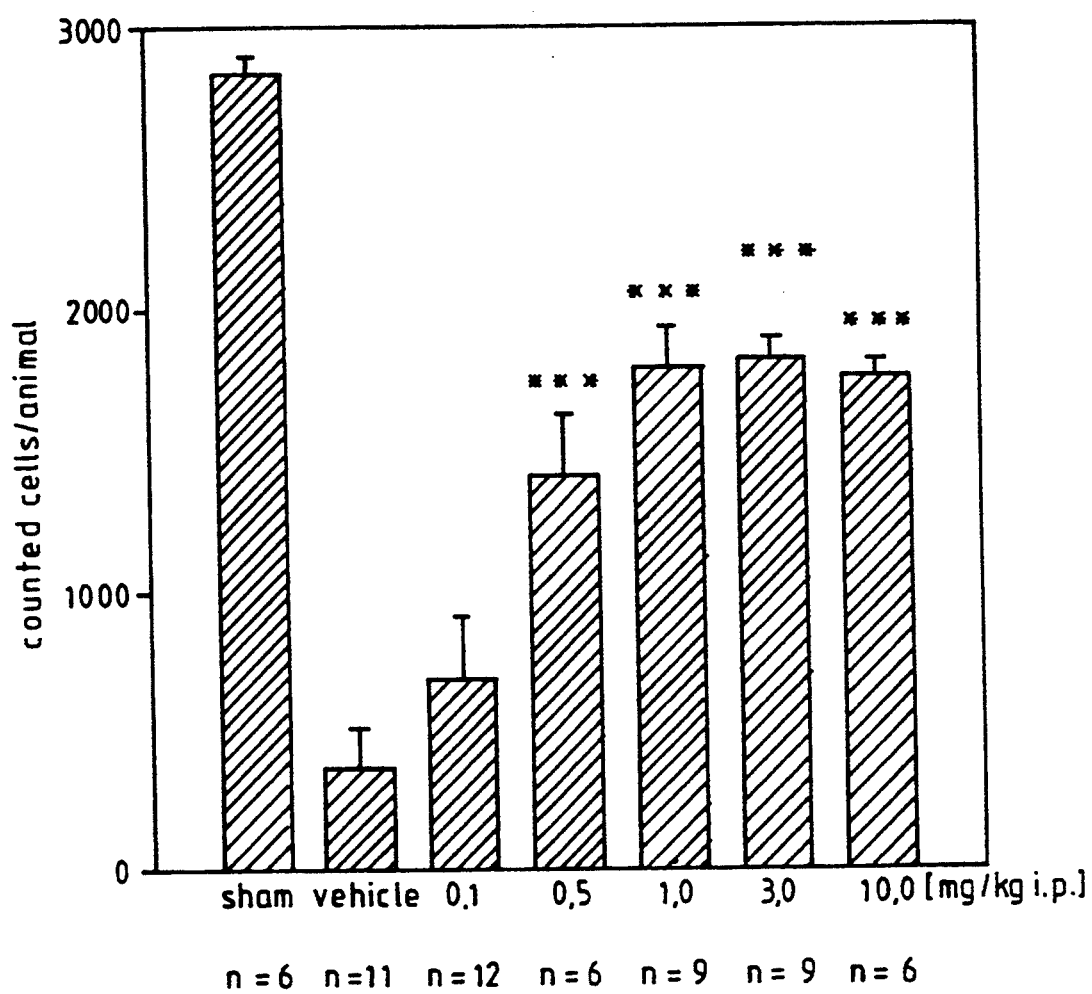
FIG. 2: shows (−)-2-[N-[4-(1,1-Dioxido-3-oxo-2,3-dihydro-benzisothiazol-2-yl)-butyl]-aminomethyl]chroman
Figure 3:
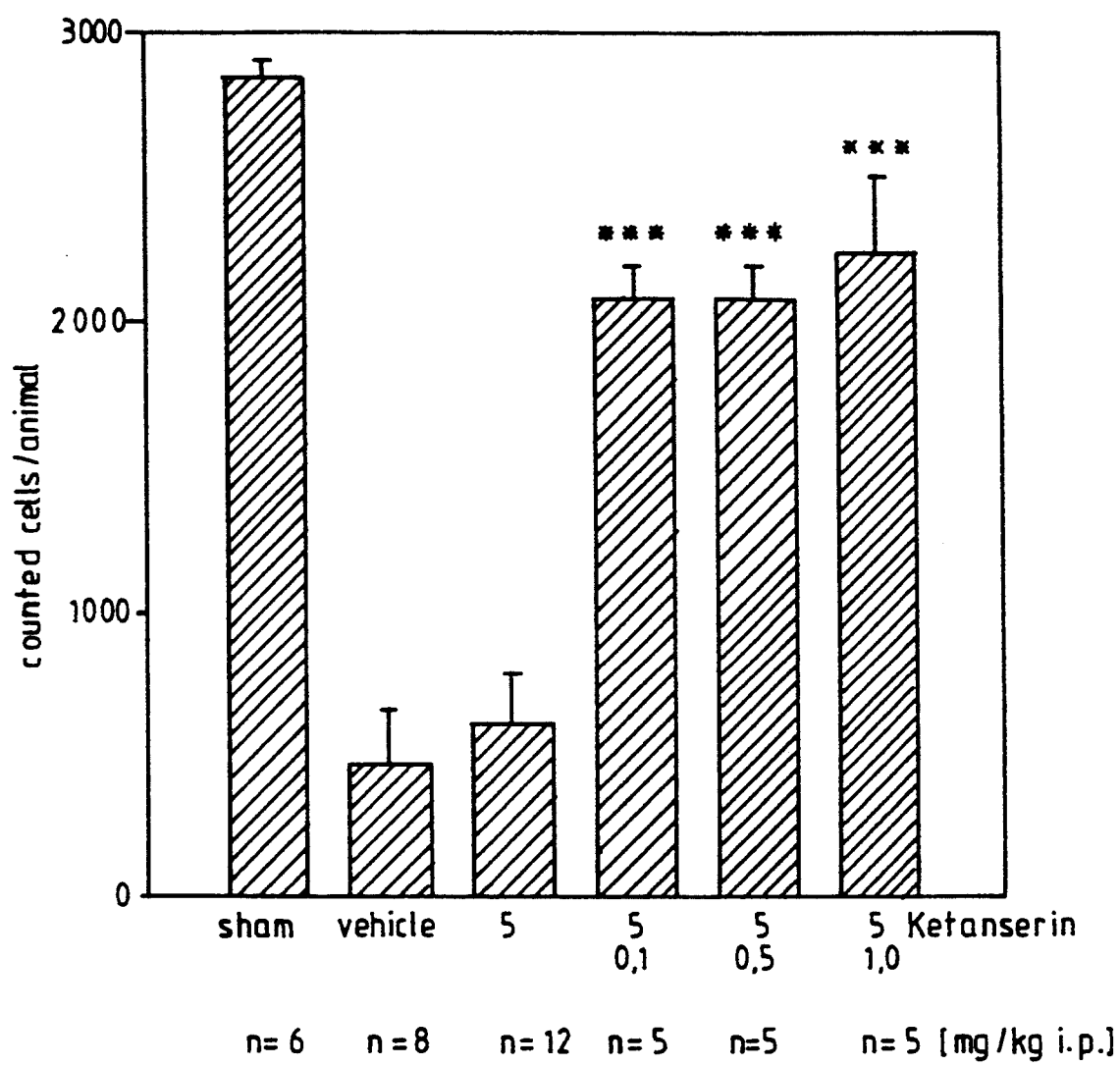
FIG. 3: shows Combination of (−)-2-[N-[4-(1,1-dioxido-3-oxo-2,3-dihydro-benzisothiazol-2-yl)butyl]-aminomethyl]chroman with ketanserin.

The mode of action of the combination according to the invention for the preventative and following treatment of cerebral ischaemias can be determined with the aid of the gerbil model of transient global fore brain ischaemia.

Test methods

For the induction of transient forebrain ischaemia, both carotid arteries in mongolian gerbils were clamped off under halothane anaesthesia (1% strength in room air) for 5 minutes. Seven days after the ischaemia, the brains of the animals were perfused transcardially for the purpose of paraffin embedding. 7 μm thick frontal sections of the brains were prepared. One section in each case was assessed microscopically from 4 different planes by means of a camera lucida projection. The pyramidal cells surviving in the CA1 region were counted inside a standardised frame. All counts were added for each animal. The significance of the differing average values was determined by a variance analysis according to Scheffe. $P<0.05$ was fixed as the significance level.

15 minutes before onset of ischaemia and twice daily on the 3 following days medicaments were injected intraperitoneally in 300 μl of 0.9% strength NaCl.

Test data

Ketanserin was administered in a dose of 5 mg/kg, which produced a submaximal effect with a 52% protection of the pyramidal cells (see figure). By addition of increasing doses of (−)-2-[N-[4-(1,1-dioxido-3-oxo-2,3-dihydro-benzisothiazol-2-yl)-butyl]aminomethyl]-chroman, the neuroprotective effect of ketanserin, even at a dose (0.1 mg/kg) at which (−)-2-[N-[4-(1,1-dioxido-3-oxo-2,3-dihydro-benzisothiazol-2-yl)-butyl]aminomethyl]chroman was inactive, was further improved.

I claim:

1. A neuroprotective composition comprising at least one aminomethyl-chroman selected from the group consisting of (+)-, (−)- or (±)-2-[N-[4-(1,1-dioxido-3-oxo-2,3-dihydro-benzisothiazol-2-yl)butyl]aminomethyl]-8-methoxy-chroman, (+)-, (−)- and (±)-2-[N-[4-(1,1-dioxido-3-oxo-2,3-dihydro-benzisothiazol-2-yl)butyl]-aminomethyl]-chroman and salts thereof as Component A and ketanserin as Component B wherein 0.01 to 100 parts by weight of Component B is present per part by weight of Component A.

2. The method of treating cerebral ischaemias in a patient in need thereof, which comprises administering to such patient an amount effective therefor of a neuroprotective composition according to claim 1.

3. A composition according to claim 1, containing about 0.1 to 10 parts by weight of B per part by weight of A.

* * * * *